United States Patent
Den Boef et al.

(10) Patent No.: US 10,067,068 B2
(45) Date of Patent: Sep. 4, 2018

(54) LITHOGRAPHIC APPARATUS AND METHOD FOR PERFORMING A MEASUREMENT

(71) Applicant: ASML Netherlands B.V., Veldhoven (NL)

(72) Inventors: Arie Jeffrey Den Boef, Waalre (NL); Simon Gijsbert Josephus Mathijssen, Rosmalen (NL); Nan Lin, Eindhoven (NL); Sander Bas Roobol, Veldhoven (NL)

(73) Assignee: ASML Netherlands B.V., Veldhoven (NL)

( * ) Notice: Subject to any disclaimer, the term of this patent is extended or adjusted under 35 U.S.C. 154(b) by 0 days.

(21) Appl. No.: 15/388,463

(22) Filed: Dec. 22, 2016

(65) Prior Publication Data

US 2017/0184511 A1 Jun. 29, 2017

(30) Foreign Application Priority Data

Dec. 23, 2015 (EP) .................................... 15202301

(51) Int. Cl.
*G03F 7/20* (2006.01)
*G03F 9/00* (2006.01)
*G01N 21/88* (2006.01)

(52) U.S. Cl.
CPC ....... *G01N 21/8806* (2013.01); *G03F 7/7065* (2013.01); *G03F 7/70191* (2013.01);
(Continued)

(58) Field of Classification Search
CPC ....... G01N 2021/8822; G01N 21/8806; G01N 2201/061; G03F 7/70191; G03F 7/70483;
(Continued)

(56) References Cited

U.S. PATENT DOCUMENTS 4,577,968 A 3/1986 Makosch
5,000,573 A 3/1991 Suzuki et al.
(Continued)

FOREIGN PATENT DOCUMENTS

TW 201546444 A 12/2015

OTHER PUBLICATIONS

International Search Report and Written Opinion of the International Searching Authority directed to related International Patent Application No. PCT/EP2016/080103, dated Feb. 21, 2017; 10 pages.
(Continued)

*Primary Examiner* — Michelle M Iacoletti
(74) *Attorney, Agent, or Firm* — Sterne, Kessler, Goldstein & Fox P.L.L.C.

(57) ABSTRACT

A lithographic apparatus is a machine that applies a desired pattern onto a substrate, usually onto a target portion of the substrate. A lithographic apparatus can be used, for example, in the manufacture of integrated circuits (ICs). The lithographic apparatus has an inspection apparatus with an illumination system that utilizes illuminating radiation with a wavelength of 2-40 nm. The illumination system includes an optical element that splits the illuminating radiation into a first and a second illuminating radiation and induces a time delay to the first or the second illuminating radiation. A detector detects the radiation that has been scattered by a target structure. The inspection apparatus has a processing unit operable to control a time delay between the first scattered radiation and the second scattered radiation so as to optimize a property of the combined first and second scattered radiation.

18 Claims, 7 Drawing Sheets

(52) U.S. Cl.
CPC ........ *G03F 7/70483* (2013.01); *G03F 9/7049* (2013.01); *G03F 9/7065* (2013.01); *G01N 2021/8822* (2013.01); *G01N 2201/061* (2013.01)

(58) Field of Classification Search
CPC ............... G03F 7/7065; G03F 7/70633; G03F 7/70683; G03F 7/705; G03F 7/70125; G03F 7/70158; G03F 7/70616; G03F 9/708; G03F 23/544
See application file for complete search history.

(56) References Cited

U.S. PATENT DOCUMENTS

| | | |
|---|---|---|
| 5,498,878 A | 3/1996 | Hasegawa et al. |
| 2006/0066855 A1 | 3/2006 | Boef et al. |
| 2008/0239318 A1 | 10/2008 | Den Boef et al. |
| 2010/0123887 A1 | 5/2010 | De Winter et al. |
| 2011/0102753 A1 | 5/2011 | Van De Kerkhof et al. |
| 2011/0292365 A1 | 12/2011 | Cramer et al. |
| 2012/0081684 A1* | 4/2012 | Den Oef ................ G01N 21/94 355/67 |
| 2012/0044470 A1 | 9/2012 | Smilde et al. |
| 2012/0242970 A1 | 9/2012 | Smilde et al. |
| 2015/0204664 A1 | 7/2015 | Bringoltz et al. |
| 2015/0346605 A1 | 12/2015 | Den Boef et al. |

OTHER PUBLICATIONS

Ku et al., "Optimal measurement method for scatterometer-based overlay metrology," Optical Engineering 47(8), 083604 (Aug. 2008); 10 pages.

\* cited by examiner

LITHOGRAPHIC APPARATUS AND METHOD FOR PERFORMING A MEASUREMENT

FIELD

The present invention relates to a lithographic apparatus and a method for performing a measurement. In particular, it relates to an inspection apparatus comprised in a lithographic apparatus, as well as a method for performing a measurement therewith.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., including part of, one, or several dies) on a substrate (e.g., a silicon wafer). Multiple layers, each having a particular pattern and material composition, are applied to define functional devices and interconnections of the finished product.

In lithographic processes, it is desirable frequently to make measurements of the structures created, e.g., for process control and verification. Various tools for making such measurements are known, including scanning electron microscopes, which are often used to measure critical dimension (CD), and specialized tools to measure overlay, the accuracy of alignment of two layers in a device. Recently, various forms of scatterometers have been developed for use in the lithographic field.

Examples of known scatterometers often rely on provision of dedicated metrology targets. For example, a method may require a target in the form of a simple grating that is large enough that a measurement beam generates a spot that is smaller than the grating (i.e., the grating is underfilled). In so-called reconstruction methods, properties of the grating can be calculated by simulating interaction of scattered radiation with a mathematical model of the target structure. Parameters of the model are adjusted until the simulated interaction produces a diffraction pattern similar to that observed from the real target.

In addition to measurement of feature shapes by reconstruction, diffraction-based overlay can be measured using such apparatus, as described in published patent application US2006066855A1. Diffraction-based overlay metrology using dark-field imaging of the diffraction orders enables overlay measurements on smaller targets. These targets can be smaller than the illumination spot and may be surrounded by product structures on a wafer. Examples of dark field imaging metrology can be found in numerous published patent applications, such as for example US2011102753A1 and US20120044470A. Multiple gratings can be measured in one image, using a composite grating target. The known scatterometers tend to use light in the visible or near-IR wave range, which requires the pitch of the grating to be much coarser than the actual product structures whose properties are actually of interest. Such product features may be defined using deep ultraviolet (DUV) or extreme ultraviolet (EUV) radiation having far shorter wavelengths. Unfortunately, such wavelengths are not normally available or usable for metrology.

On the other hand, the dimensions of modern product structures are so small that they cannot be imaged by optical metrology techniques. Small features include for example those formed by multiple patterning processes, and/or pitch-multiplication. Hence, targets used for high-volume metrology often use features that are much larger than the products whose overlay errors or critical dimensions are the property of interest. The measurement results are only indirectly related to the dimensions of the real product structures, and may be inaccurate because the metrology target does not suffer the same distortions under optical projection in the lithographic apparatus, and/or different processing in other steps of the manufacturing process. While scanning electron microscopy (SEM) is able to resolve these modern product structures directly, SEM is much more time consuming than optical measurements. Moreover, electrons are not able to penetrate through thick process layers, which makes them less suitable for metrology applications. Other techniques, such as measuring electrical properties using contact pads is also known, but it provides only indirect evidence of the true product structure.

By decreasing the wavelength of the radiation used during metrology (i.e. moving towards the "soft X-ray" wavelength spectrum), the measurement performance improves since the radiation can penetrate further into the product structures. However, this requires a corresponding improvement in the spectral resolution of the metrology system. Additionally, the complexity of product structures is increasing, with product structures comprising increasing numbers of layers and a corresponding increase in thickness. This, in turn, increases the spectral resolution required to perform metrology measurements.

SUMMARY

The present invention aims to provide an alternative inspection apparatus and method for performing measurements of the type described above.

The inventors have determined that by providing a time-delayed copy of the illuminating radiation used in the inspection apparatus, the necessary spectral resolution of the metrology system to carry out metrology on product structures can be reduced.

According to a first aspect of the present invention, there is provided a method of performing a measurement in an inspection apparatus, comprising:
  providing an illumination radiation;
  illuminating a target structure with the illuminating radiation resulting in at least a first and a second scattered radiation; and
  detecting combined first and second scattered radiation; and
  controlling a time delay between the first scattered radiation and the second scattered radiation so as to optimize a property of the combined first and second scattered radiation.

According to a second aspect of the present invention, there is provided an inspection apparatus, comprising:
  a radiation source operable to provide an illumination radiation;
  an illumination system operable to illuminate a target structure with the illuminating radiation resulting in at least a first and a second scattered radiation;
  a detector operable to detect combined first and second scattered radiation; and
  a processing unit operable to control a time delay between the first scattered radiation and the second scattered radiation so as to optimize a property of the combined first and second scattered radiation.

The invention yet further provides a lithographic apparatus comprising an inspection apparatus according to the invention as set forth above.

The invention yet further provides a substrate for use in performing a measurement in an inspection apparatus, the substrate comprising a target structure for use in a method according to the invention as set forth above.

The invention yet further provides a method for a lithographic apparatus for manufacturing substrates according to the invention as set forth above.

The invention yet further provides a computer program product containing one or more sequences of machine-readable instructions for implementing controlling steps in a method according to the invention as set forth above.

Further aspects, features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION OF EXEMPLARY EMBODIMENTS

Before describing embodiments of the invention in detail, it is instructive to present an example environment in which embodiments of the present invention may be implemented.

Figure 1:
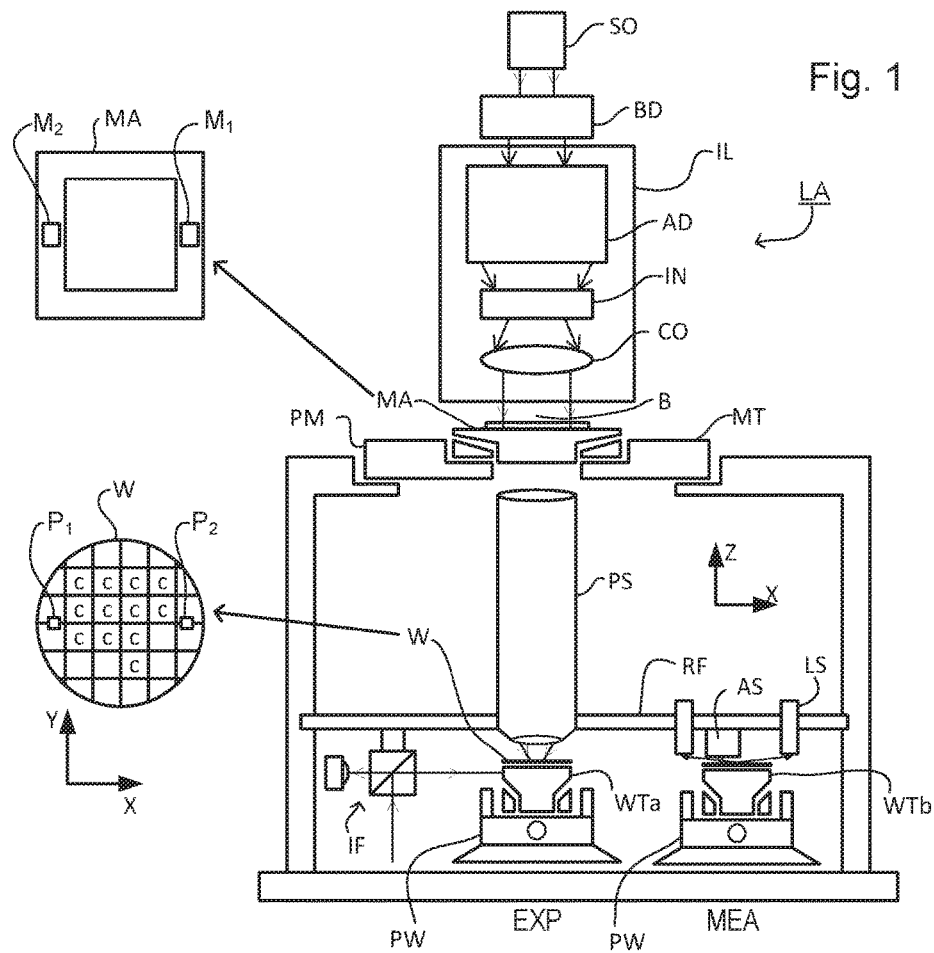
FIG. 1 depicts a lithographic apparatus.

FIG. 1 schematically depicts a lithographic apparatus LA. The apparatus includes an illumination system (illuminator) IL configured to condition a radiation beam B (e.g., UV radiation or DUV or EUV radiation), a patterning device support or support structure (e.g., a mask table) MT constructed to support a patterning device (e.g., a mask) MA and connected to a first positioner PM configured to accurately position the patterning device in accordance with certain parameters; two substrate tables (e.g., a wafer table) WTa and WTb each constructed to hold a substrate (e.g., a resist coated wafer) W and each connected to a second positioner PW configured to accurately position the substrate in accordance with certain parameters; and a projection system (e.g., a refractive projection lens system) PS configured to project a pattern imparted to the radiation beam B by patterning device MA onto a target portion C (e.g., including one or more dies) of the substrate W. A reference frame RF connects the various components, and serves as a reference for setting and measuring positions of the patterning device and substrate and of features on them.

The illumination system may include various types of optical components, such as refractive, reflective, magnetic, electromagnetic, electrostatic or other types of optical components, or any combination thereof, for directing, shaping, or controlling radiation.

The patterning device support holds the patterning device in a manner that depends on the orientation of the patterning device, the design of the lithographic apparatus, and other conditions, such as for example whether or not the patterning device is held in a vacuum environment. The patterning device support can use mechanical, vacuum, electrostatic or other clamping techniques to hold the patterning device. The patterning device support MT may be a frame or a table, for example, which may be fixed or movable as required. The patterning device support may ensure that the patterning device is at a desired position, for example with respect to the projection system.

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

As here depicted, the apparatus is of a transmissive type (e.g., employing a transmissive patterning device). Alternatively, the apparatus may be of a reflective type (e.g., employing a programmable mirror array of a type as referred to above, or employing a reflective mask). Examples of patterning devices include masks, programmable mirror arrays, and programmable LCD panels. Any use of the terms "reticle" or "mask" herein may be considered synonymous with the more general term "patterning device." The term "patterning device" can also be interpreted as referring to a device storing in digital form pattern information for use in controlling such a programmable patterning device.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems.

In operation, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD including, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may for example include an adjuster AD for adjusting the angular intensity distribution of the radiation beam, an integrator IN and a condenser CO. The illuminator may be used to condition the radiation beam, to have a desired uniformity and intensity distribution in its cross section.

The radiation beam B is incident on the patterning device MA, which is held on the patterning device support MT, and is patterned by the patterning device. Having traversed the patterning device (e.g., mask) MA, the radiation beam B passes through the projection system PS, which focuses the beam onto a target portion C of the substrate W. With the aid of the second positioner PW and position sensor IF (e.g., an interferometric device, linear encoder, 2-D encoder or capacitive sensor), the substrate table WTa or WTb can be moved accurately, e.g., so as to position different target portions C in the path of the radiation beam B. Similarly, the first positioner PM and another position sensor (which is not explicitly depicted in FIG. 1) can be used to accurately position the patterning device (e.g., mask) MA with respect to the path of the radiation beam B, e.g., after mechanical retrieval from a mask library, or during a scan.

Patterning device (e.g., mask) MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the patterning device (e.g., mask) MA, the mask alignment marks may be located between the dies. Small alignment mark may also be included within dies, in amongst the device features, in which case it is desirable that the markers be as small as possible and not require any different imaging or process conditions than adjacent features. The alignment system, which detects the alignment markers is described further below.

The depicted apparatus could be used in a variety of modes. In a scan mode, the patterning device support (e.g., mask table) MT and the substrate table WT are scanned synchronously while a pattern imparted to the radiation beam is projected onto a target portion C (i.e., a single dynamic exposure). The speed and direction of the substrate table WT relative to the patterning device support (e.g., mask table) MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion. Other types of lithographic apparatus and modes of operation are possible, as is well-known in the art. For example, a step mode is known. In so-called "maskless" lithography, a programmable patterning device is held stationary but with a changing pattern, and the substrate table WT is moved or scanned.

Combinations and/or variations on the above described modes of use or entirely different modes of use may also be employed.

Lithographic apparatus LA is of a so-called dual stage type which has two substrate tables WTa, WTb and two stations—an exposure station EXP and a measurement station MEA—between which the substrate tables can be exchanged. While one substrate on one substrate table is being exposed at the exposure station, another substrate can be loaded onto the other substrate table at the measurement station and various preparatory steps carried out. This enables a substantial increase in the throughput of the apparatus. The preparatory steps may include mapping the surface height contours of the substrate using a level sensor LS and measuring the position of alignment markers on the substrate using an alignment sensor AS. If the position sensor IF is not capable of measuring the position of the substrate table while it is at the measurement station as well as at the exposure station, a second position sensor may be provided to enable the positions of the substrate table to be tracked at both stations, relative to reference frame RF. Other arrangements are known and usable instead of the dual-stage arrangement shown. For example, other lithographic apparatuses are known in which a substrate table and a measurement table are provided. These are docked together when performing preparatory measurements, and then undocked while the substrate table undergoes exposure.

Figure 2:
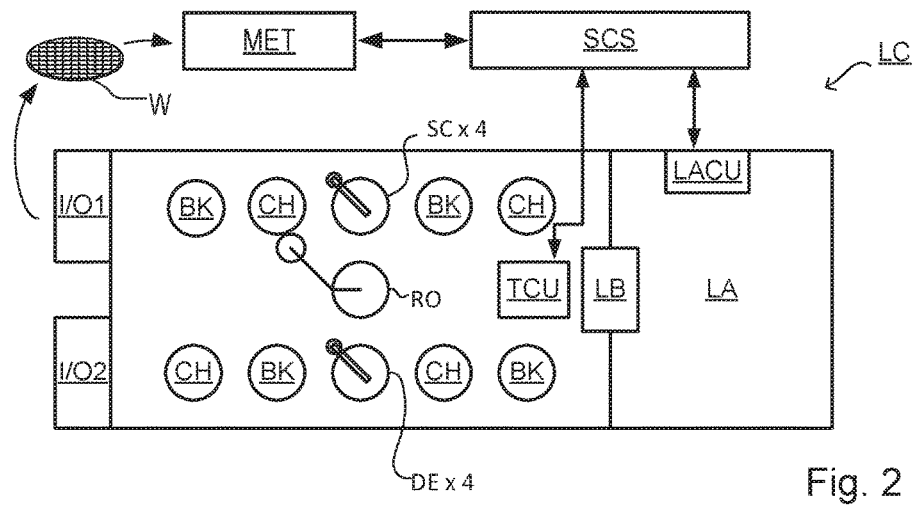
FIG. 2 depicts a lithographic cell or cluster in which an inspection apparatus according to the present invention may be used.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

The substrates processed by the track are then transferred to other processing tools for etching and other chemical or physical treatments within the device manufacturing process. In some instances, metrology may be performed on substrates after such etching or chemical/physical treatment steps.

The lithographic apparatus control unit LACU controls all the movements and measurements of the various actuators and sensors described. LACU also includes signal processing and data processing capacity to implement desired calculations relevant to the operation of the apparatus. In the terminology of the introduction and claims, the combination of these processing and control functions referred to simply as the "controller". In practice, control unit LACU will be realized as a system of many sub-units, each handling the real-time data acquisition, processing and control of a subsystem or component within the apparatus. For example, one processing subsystem may be dedicated to servo control of the substrate positioner PW. Separate units may even handle coarse and fine actuators, or different axes. Another unit might be dedicated to the readout of the position sensor IF. Overall control of the apparatus may be controlled by a central processing unit, communicating with these subsystems processing units, with operators and with other apparatuses involved in the lithographic manufacturing process.

Figure 3A:
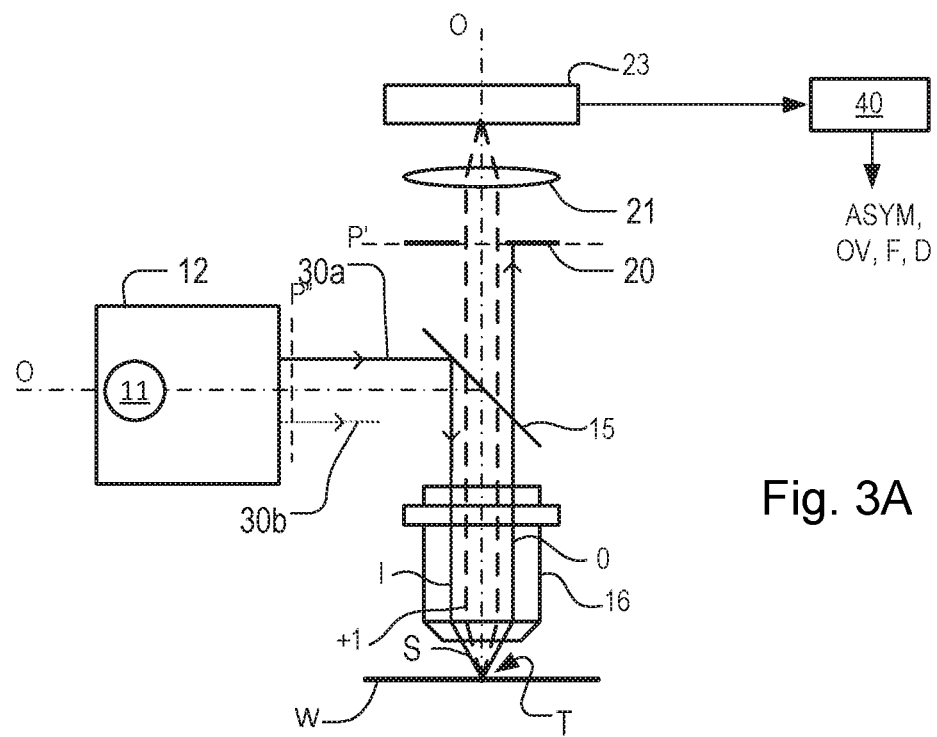
FIGS. 3A-3B illustrate schematically an inspection apparatus adapted to perform a known dark-field imaging inspection methods.

FIG. 3(a) shows schematically the key elements of an inspection apparatus implementing so-called dark field imaging metrology. The apparatus may be a stand-alone device or incorporated in either the lithographic apparatus LA, e.g., at the measurement station, or the lithographic cell LC. An optical axis, which has several branches throughout the apparatus, is represented by a dotted line O. A target grating structure T and diffracted rays are illustrated in more detail in FIG. 3(b).

As described in the prior applications cited in the introduction, the dark-field-imaging apparatus of FIG. 3(a) may be part of a multi-purpose angle-resolved scatterometer that may be used instead of or in addition to a spectroscopic scatterometer. In this type of inspection apparatus, radiation emitted by a radiation source 11 is conditioned by an illumination system 12. For example, illumination system 12 may include a collimating lens system, a color filter, a polarizer and an aperture device. The conditioned radiation follows an illumination path, in which it is reflected by partially reflecting surface 15 and focused into a spot S on substrate W via a microscope objective lens 16. A metrology target T may be formed on substrate W. Lens 16, has a high numerical aperture (NA), preferably at least 0.9 and more preferably at least 0.95. Immersion fluid can be used to obtain with numerical apertures over 1 if desired. The multi-purpose scatterometer may have two or more measurement branches. Additionally, further optical systems and branches will be included in a practical apparatus, for example to collect reference radiation for intensity normalization, for coarse imaging of capture targets, for focusing and so forth. Details of these can be found in the prior publications mentioned above. For the purposes of the present disclosure, only the measurement branch of interest for the dark-filed imaging metrology is illustrated and described in detail.

In the collection path for dark-field imaging, imaging optical system 21 forms an image of the target on the substrate W on sensor 23 (e.g. a CCD or CMOS sensor). An aperture stop 20 is provided in a plane P' in the collection path. Plane P' is a plane conjugate to a pupil plane P (not shown) of objective lens 16. Aperture stop 20 may also be called a pupil stop. Aperture stop 20 can take different forms, just as the illumination aperture can take different forms. The aperture stop 20, in combination with the effective aperture of lens 16, determines what portion of the scattered radiation is used to produce the image on sensor 23. Typically, aperture stop 20 functions to block the zeroth order diffracted beam so that the image of the target formed on sensor 23 is formed only from the first order beam(s). In an example where both first order beams are combined to form an image, this would be the so-called dark field image, equivalent to dark-field microscopy. In the present application, however, only one of the first orders is imaged at a time, as explained below. The images captured by sensor 23 are output to image processor and controller 40, the function of which will depend on the particular type of measurements being performed. For the present purpose, measurements of asymmetry of the target structure are performed. Asymmetry measurements can be combined with knowledge of the target structures to obtain measurements of performance parameters of lithographic process used to form them. Performance parameters that can be measured in this way include for example overlay, focus and dose.

Where a metrology target T is provided on substrate W, this may be a 1-D grating, which is printed such that after development, the bars are formed of solid resist lines. The target may be a 2-D grating, which is printed such that after development, the grating is formed of solid resist pillars or vias in the resist. The bars, pillars or vias may alternatively be etched into the substrate. Each of these gratings is an example of a target structure whose properties may be investigated using the inspection apparatus.

The various components of illumination system 12 can be adjustable to implement different metrology 'recipes' within the same apparatus. In addition to selecting wavelength (color) and polarization as characteristics of the particular, illumination system 12 can be adjusted to implement different illumination profiles. Because plane P" is conjugate with pupil plane P of objective lens 16 and the plane of the detector 19, an illumination profile in plane P" defines the angular distribution of light incident on substrate W in spot S. To implement different illumination profiles, an aperture device can be provided in the illumination path. The aperture device may comprise different apertures mounted on a movable slide or wheel. It may alternatively comprise a programmable spatial light modulator. As a further alternative, optical fibers may be disposed at different location in the plane P" and used selectively to deliver light or not deliver light at their respective locations. These variants are all discussed and exemplified in the documents cited above.

In a first example illumination mode, rays 30a are provided so that the angle of incidence is as shown at 'I' and the path of the zero order ray reflected by target T is labeled '0' (not to be confused with optical axis 'O'). In a second illumination mode, rays 30b can be provided, in which case the angles of incidence and reflection will be swapped. Both of these illumination modes will be recognized as off-axis illumination modes. Many different illumination modes can be implemented for different purposes.

Figure 3B:
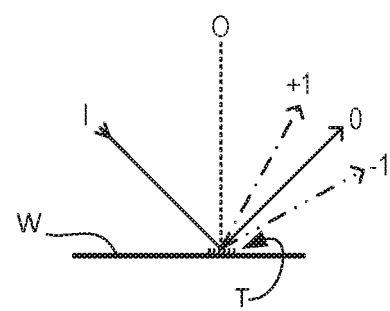

As shown in more detail in FIG. 3(b), target grating T as an example of a target structure is placed with substrate W normal to the optical axis O of objective lens 16. In the case of an off-axis illumination profile, a ray of illumination I impinging on grating T from an angle off the axis O gives rise to a zeroth order ray (solid line O) and two first order rays (dot-chain line+1 and double dot-chain line−1). It should be remembered that with an overfilled small target grating, these rays are just one of many parallel rays covering the area of the substrate including metrology target grating T and other features. Since the beam of illuminating rays 30a has a finite width (necessary to admit a useful quantity of light), the incident rays I will in fact occupy a range of angles, and the diffracted rays 0 and +1/−1 will be spread out somewhat. According to the point spread function of a small target, each order +1 and −1 will be further spread over a range of angles, not a single ideal ray as shown.

Referring also to FIG. 3(a), under the first illumination mode with rays 30a, +1 order diffracted rays from the target grating will enter the objective lens 16 and contribute to the image recorded at sensor 23. When the second illumination mode is used, rays 30b are incident at an angle opposite to rays 30b, and so the −1 order diffracted rays enter the objective and contribute to the image. Aperture stop 20 blocks the zeroth order radiation when using off-axis illumination. As described in the prior publications, illumination modes can be defined with off-axis illumination in X and Y directions.

By comparing images of the target grating under these different illumination modes, asymmetry measurements can be obtained. Alternatively, asymmetry measurements could be obtained by keeping the same illumination mode, but rotating the target. While off-axis illumination is shown, on-axis illumination of the targets may instead be used and a modified, off-axis aperture 20 could be used to pass substantially only one first order of diffracted light to the sensor. In a further example, prisms are used in place of aperture stop 20 which have the effect of diverting the +1 and −1 orders to different locations on sensor 23 so that they can be detected and compared without the need for two sequential image capture steps. This technique, is disclosed in the above-mentioned published patent application US2011102753A1, the contents of which are hereby incorporated by reference. 2nd, 3rd and higher order beams (not shown in FIG. 3) can be used in measurements, instead of or in addition to the first order beams. As a further variation, the off-axis illumination mode can be kept constant, while the target itself is rotated 180 degrees beneath objective lens 16 to capture images using the opposite diffraction orders.

The above techniques are typically performed using radiation with a visible wavelength. As such, the scatterometry targets have a pitch that is larger than that of the product structures on the substrate. As an example, a scatterometry target may have a target grating pitch measured in microns (µm), whereas product structures on the same substrate may have a pitch measured in nanometers (nm).

This difference in pitch induces an offset between the measured overlay and the actual overlay on the product structures. The offset is at least partly due to optical projection distortions in the lithographic apparatus and/or different processing in other steps of the manufacturing process. Presently, the offset comprises a significant contribution to the overall measured overlay. Reducing or eliminating it will therefore improve overall overlay performance.

In order to perform diffraction-based measurements on structures with a pitch corresponding to that of a product structure, it is necessary to use radiation with a shorter wavelength than visible light. However, a number of materials, such as polycrystalline silicon or amorphous carbon, which are presently used in many layers of product structures absorb ultraviolet radiation. It has, however, been found that absorption losses for radiation in the "soft X-ray" spectrum (approximately 2 nm-40 nm) is much lower than for ultraviolet radiation. It should of course be noted that the specific absorbance of a product structure is dependent on the specific materials used in the layers. Given knowledge of the properties of the materials used in a particular structure, it is possible to select the radiation wavelength used so as to minimize absorption losses.

In order to maximize the accuracy of a diffraction-based measurement, e.g. to determine overlay error, it is necessary to optimize the properties of the radiation that arrives at the detector. The property of the scattered radiation is dependent the properties of the radiation used and the properties of the structure under measurement. One parameter that may be used to describe the quality of the scattered radiation is the so-called "stack sensitivity". This parameter describes the strength of an the measured asymmetry caused by an upper target grating shifting relative to a lower target grating. It has been found that the "stack sensitivity" varies periodically in dependence on the wavelength of the radiation and the thickness of the target structure. The period of the variation can be described as:

$$\Delta \lambda = \frac{\lambda^2}{2T} \tag{1}$$

λ is the wavelength of the radiation, and T is the optical thickness of the structure being measured. An exemplary optical thickness of a product structure may be 400 nm, and an exemplary radiation wavelength may be λ=13 nm. In this example, the period of the "stack sensitivity" variation is therefore Δλ=0.23 nm.

In order to optimize the radiation measured at the detector, it is necessary for the inspection apparatus to have a spectral resolution that is better than the size of the periodic variations of the stack sensitivity. Specifically, in order to fully resolve the periodic variations of the stack sensitivity, the spectral resolution of the inspection apparatus should be at least double that of the period of the variations. In the present example, the required spectral resolution for the inspection apparatus would therefore be 0.1 nm.

The spectral resolution of an inspection apparatus, such as the one illustrated in FIG. 3, is determined by the properties of the optical system and the properties of the target structure. Due to target size constraints, the spot diameter of a typical inspection apparatus is limited to approximately 2 µm. Assuming that the illuminating radiation is a Gaussian beam, the following relation between the beam waist diameter D and the numerical aperture of the illuminating radiation NA can be derived:

$$D = \frac{2}{\pi} \frac{\lambda}{NA} \tag{2}$$

For illuminating radiation with a wavelength of λ=13 nm, the numerical aperture can be derived as NA=4 mrad.

Presently, the pitch of product structures is approximately P=40 nm. The spectral resolution of a diffraction-based inspection apparatus (e.g. a scatterometer) measuring a target structure with this pitch can be derived as: Δλ≈2P× NA=80×0.004=0.32 nm. The spectral resolution provided by the inspection apparatus is larger than the required 0.1 nm. In other terms, it is not possible to adequately resolve the periodic variations of the stack sensitivity. It is possible to improve the spectral resolution of the inspection apparatus by reducing the size of the numerical aperture. However, this will in turn require the target size to be increased. This is because a decrease in NA will result in a larger spot diameter. As discussed above, targets must be "underfilled" (i.e. the spot diameter is smaller than the size of the target). If the spot diameter is increased, the size of the target must therefore also be increased proportionally. Larger targets take up more space on the surface of a substrate, which is undesirable in a production environment since it increases the per-product manufacturing costs. In the following, a method and apparatus that improves the spectral resolution of the inspection apparatus will be described.

Figure 4:
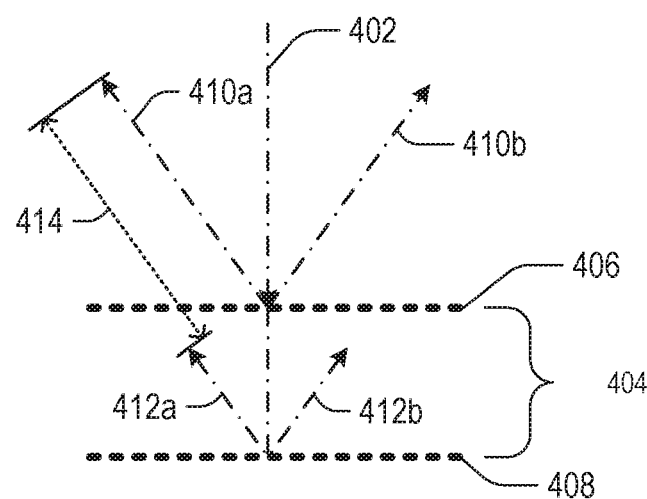
FIG. 4 is a schematic diagram of illuminating radiation and scattered radiation on a target.

FIG. 4 shows illuminating radiation 402 illuminating a target 404. The target comprises a first target structure (upper grating 406) and a second target structure (lower grating 408). The upper grating scatters the illuminating radiation 402 into distinct diffractive orders (as explained above with reference to FIG. 3(b)). For the sake of simplicity, only the −1 and +1 diffraction orders are shown in FIG. 4: 410a and 410b, which refer to the intensity of the −1 and +1 diffraction orders respectively. The lower grating, similarly, scatters the illuminating radiation into a −1 diffraction order 412a and a +1 diffraction order 412b. The radiation scattered by the lower grating is delayed relative to the radiation scattered by the upper grating by a time delay τ (reference numeral 414 in FIG. 4) due to the illuminating radiation having to travel through the target. In the present example, the time delay can be described as τ=2T/c, where c is the speed of light and T is the optical thickness of the target (it is, for exemplary purposes only, assumed that the lower grating is positioned in the bottom layer of the target, such that the illuminating radiation propagates through the entirety of the target).

As previously discussed, the −1 and +1 diffraction orders of the radiation scattered by the target are measured using a scatterometer. The complex amplitudes of the measured scattered radiation may be expressed as:

$$E_{\pm 1}(t) = A_{\pm 1} E_i(t) + B_{-1} E_i(t-\tau) \quad (3)$$

where A±1 refers to the +1 and −1 diffraction orders of the radiation scattered by the upper grating 406 respectively (i.e. 410a and 410b in FIG. 4), and B±1 refers to the +1 and −1 diffraction orders of the radiation scattered by the lower grating 408 respectively (i.e. 412a and 412b in FIG. 4). Ei is the complex amplitude of the illuminating radiation, and is given as $E_i(t) = E\exp(j\Omega t)$. The measured intensity of the scattered radiation is given by $|E_{\pm 1}(t)|^2$. It can be shown that this intensity includes a coupling term between the upper grating and the lower grating that varies periodically as $\cos(\Omega\tau)$, where Ω is the optical angular frequency of the radiation.

The principle of an exemplary apparatus will now be explained with reference to FIG. 5. For ease of comparison with FIG. 4, some parts of FIG. 5 are labeled with reference signs similar to those used in FIG. 4.

Figure 5:
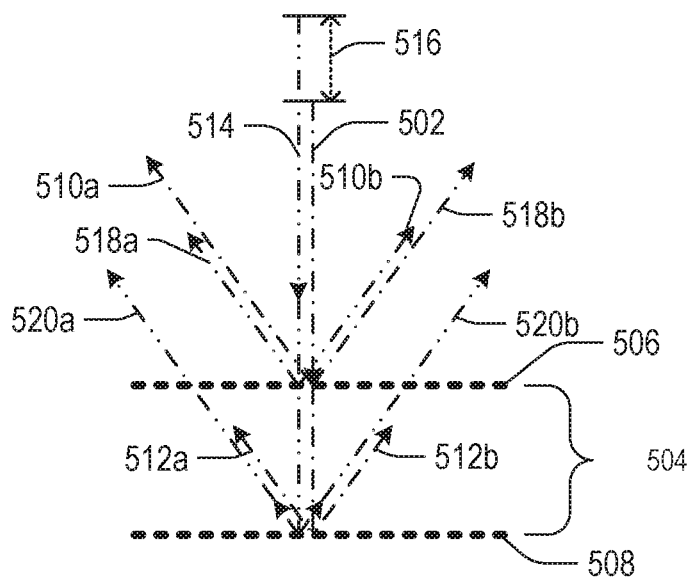
FIG. 5 is a schematic diagram of illuminating radiation and scattered radiation on a target according to a first embodiment of the invention.

In FIG. 5, in addition to the illuminating radiation 502 (Ei), a time-delayed copy of the illuminating radiation 514 (Ei(t−τi)), which has a time delay 516 (τi), is used to illuminate the target 404.

The illuminating radiation 502 is scattered by the upper grating 506 into −1 and +1 diffraction orders 510a and 510b, which refer to the intensity of the −1 and +1 diffraction orders respectively. The lower grating 508, similarly, scatters the illuminating radiation 502 into a −1 diffraction order 512a and a +1 diffraction order 512b. In an analogous fashion, the time-delayed illuminating radiation 514 is scattered by the upper grating into −1 and +1 diffraction orders 518a and 518b. The lower grating scatters the time-delayed illuminating radiation into −1 and +1 diffraction orders 520a and 520b. In this example, equation (3) can be rewritten as:

$$E_{\pm 1} = A_{\pm 1} E_i(t) + B_{\pm 1} E_i(t-\tau) + A_{\pm 1} E_i(t-\tau_i) + B_{\pm 1} E_i(t-\tau-\tau_i) \quad (4)$$

In this example, the complex amplitude contains four coupling terms that describe the coupling between the upper grating 506 and the lower grating 508. Three of these terms vary rapidly as a function of Ω, and will accordingly be averaged out to zero during detection. The last term, however, has a variation given by $\cos(\Omega(\tau-\tau_i))$. This variation has a lower frequency than the one described with reference to FIG. 4.

The period of the "stack sensitivity" can, in this example, be expressed as:

$$\Delta\lambda = \frac{\lambda^2}{2T - L_i} \quad (5)$$

Li is the total path difference introduced between the first and the second illumination radiation. From equation (5) it can be seen that, when compared with equation (1) above, the period of the "stack sensitivity" increases when a path difference, i.e. a time delay, is introduced. By controlling the time delay, the period can therefore be increased so as to be resolvable by the spectral resolution of the inspection apparatus.

Figure 6:
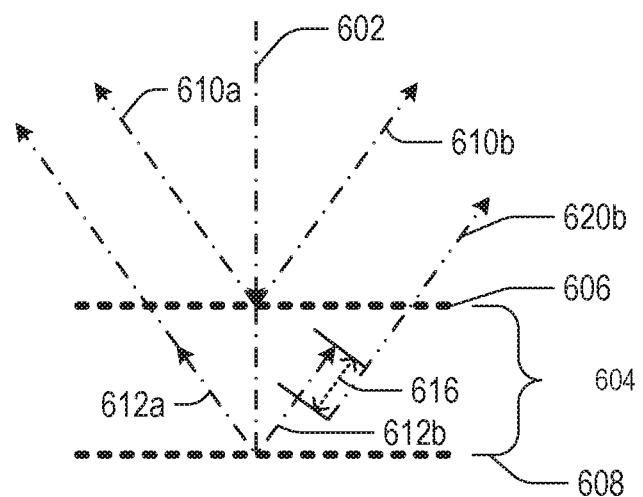
FIG. 6 is a schematic diagram of illuminating radiation and scattered radiation on a target according to a second embodiment of the invention.

FIG. 6 shows a second exemplary principle. For ease of comparison with FIG. 5, some parts of FIG. 6 are labeled with reference signs similar to those used in FIG. 5. In the example shown in FIG. 5, the time-delay is introduced to the illuminating radiation, i.e. before the radiation is scattered by the target. However, it is equally feasible to introduce the time delay to the scattered radiation, i.e. after the radiation is scattered by the target, as will now be discussed. In this example, the time delay 616 is introduced on the radiation scattered by the lower grating 50. In the second exemplary principle, at least one of the −1 diffraction order 620a or +1 diffraction order 620b scattered by the lower grating 608 has a time delay 616 introduced to it. In FIG. 6, only the +1 diffraction order is shown as having a time delay, but it will be appreciated that either or both of the −1 and +1 diffraction orders could have a time delay introduced to it. Additionally, it will be appreciated that, while FIG. 6 shows that the time delay is introduced to the +1 diffraction order 620b scattered by the lower grating, it is equally possible to introduce the time delay to the diffraction order 610b scattered by the upper grating. Furthermore, it is, in principle, also possible to introduce time delays to any combination of the +1 or −1 diffraction orders scattered by either or both of the upper and lower gratings.

Some of the coupling terms of the complex amplitude of the detected scattered radiation differ from those shown in equation (4) above. However, as described above, most of the coupling terms vary rapidly as a function of Ω, and will accordingly be averaged out to zero during detection. The remaining coupling term is substantially identical to the final coupling term of equation (4), and the "stack sensitivity" can therefore be determined in a similar fashion as described with reference to FIG. 5 above.

Figure 7:
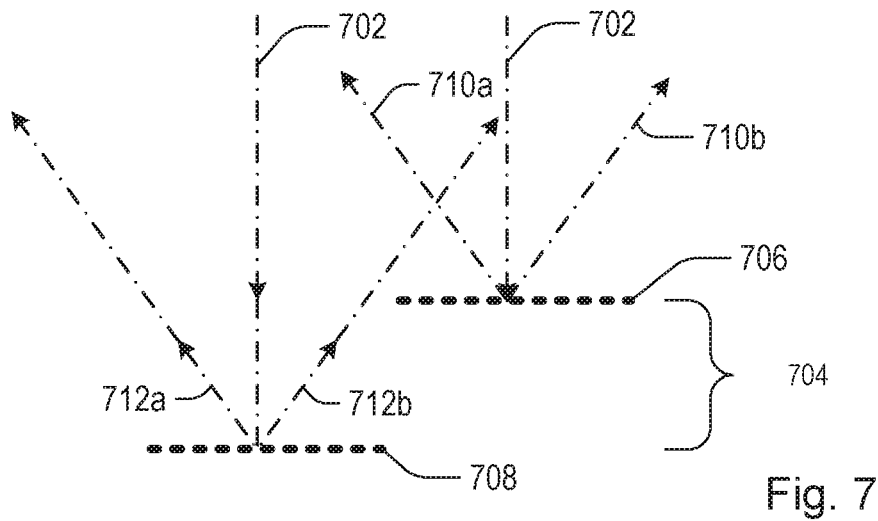
FIG. 7 is a schematic diagram of illuminating radiation and scattered radiation on a target according to a third embodiment of the invention.

In the above examples, the upper grating and the lower grating substantially overlap. Using two illumination radiation beams will reduce the contrast in the resulting measurement due to the increased background signal. This can be avoided by spatially separating the upper grating and the lower grating as illustrated in FIG. 7. Illuminating radiation 702 illuminates a target 704 that comprises an upper grating 406 and a lower grating 708. The upper grating scatters the illuminating radiation 702 into −1 and +1 diffraction orders 410a and 410b (respectively). The lower grating, similarly, scatters the illuminating radiation 702 into a −1 diffraction order 712a and a +1 diffraction order 712b.

As the upper and lower gratings are spatially separated, an offset is introduced to the asymmetry measurement, which must be corrected. A number of well-known methods can be used to correct for this offset, for example as described in published patent applications US20080239318 A1, US20110292365 A1 or US20120242970 A1.

Figure 8:
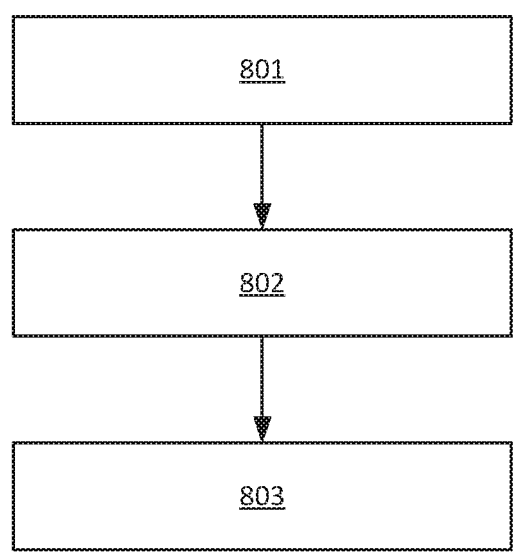
FIG. 8 schematically illustrates a method according to an embodiment of the invention.

An exemplary method of performing a measurement will now be described with reference to FIG. 8. In a first step 801, illuminating radiation is provided by an illumination system. The radiation may have any suitable wavelength. In one example, the radiation wavelength may be within the range 2 nm-40 nm. In a specific example, the wavelength is 13 nm. In another example, the radiation wavelength may be substantially within the visible spectrum. It will be appreciated that the radiation wavelength may be chosen so as to optimize the radiation of interest or reduce the amount of radiation being absorbed by the target under measurement. Although reference is made to "illuminating radiation", it is to be understood that the illuminating radiation may comprise one or several illumination beams. In one example, the illuminating radiation may comprise a first and a second illuminating radiation beam (in the following, the terms illuminating radiation and illuminating radiation beam will be used interchangeably). The first and second illuminating radiation may in some examples be combined into a combined illuminating radiation. In yet other examples comprise a plurality of individual illuminating radiation beams.

In a second step 802, the illuminating radiation is used to illuminate a target structure resulting in at least a first and a second scattered radiation. The target structure may in some examples be a dedicated target structure, such as a target grating with a pitch similar to the pitch of product structures. In other examples, the target structure may be a product structure (e.g. a memory device). The target structure may in some examples comprise a first target and a second target. In one example, the first scattered radiation comprises illuminating radiation scattered by the first target. In another example, the second scattered radiation comprises illuminating radiation scattered by the second target. Both of the first target and the second target may be illuminated by the whole of the illuminating radiation or only by a portion thereof. For example, if the illuminating radiation is comprised of first and second illuminating radiation, the first illuminating radiation may illuminate the first target and the second illuminating radiation may illuminate the second target.

In a third step 803, combined first and second scattered radiation is detected and a time delay between the first scattered radiation and the second scattered radiation is controlled so as to optimize a property of the combined first and second scattered radiation. The time delay may be controlled in any suitable manner. As discussed above, with reference to FIGS. 5 and 6, it does not matter, in principle, whether the time delay is introduced before or after the radiation is scattered by the target. In one example, the time delay may be controlled by actuating an optical component located in the beam path of the illuminating radiation. In another example, the time delay may be controlled by actuating an optical component located in the beam path of the first or second scattered radiation. In yet another example, the time delay may be controlled by controlling the phase of the first or second illuminating radiation relative to the second or first illuminating radiation respectively.

A first example of an illumination system 900 in which at least part of the above method may be implemented will now be described with reference to FIG. 9. The illumination system may for example be used in place of illumination system 12 in the inspection apparatus shown in FIG. 3(a). It should be noted that the present example utilizes the exemplary principle discussed with reference to FIG. 5, wherein the time delay is introduced to the illuminating radiation. The illumination system is a so-called High Harmonic Generation system, although it should be noted that this is for exemplary purposes only. Several types of illumination system may be envisaged. A radiation source (not shown) emits radiation beam 902 with a particular wavelength. In the present example, the radiation source is a femtosecond laser emitting illuminating radiation having an infrared wavelength. The radiation propagates to a first optical element 904, which comprises an optical wedge, which comprises a first optical wedge portion 906, a second optical wedge portion 908 and a stop 910. The stop is positioned so that it blocks the central portion of the radiation beam 902, thereby splitting the radiation beam into first radiation 912 and second radiation 914.

The first and second radiation propagate through a gas 918. The first optical wedge portion 806 and lens 816 cooperate to focus the first radiation 912 into a first spot 920 inside the gas. Similarly, second optical wedge portion 908 and lens 916 cooperate to focus the second radiation 914 into a second spot 922 inside the gas jet.

The first radiation and the second radiation interact with the gas to provide first illuminating radiation 924 and second illuminating radiation 926. The illuminating radiation passes through an optical element 928 that suppresses unwanted radiation wavelengths. In the present example, the optical element is an infra-red suppressing filter. The illuminating radiation subsequently illuminates a target structure provided on a substrate 930. In the present example, the target structure comprises a first target and a second target that are spatially separated in the plane of the substrate. The first illuminating radiation illuminates the first target portion and the second illuminating radiation illuminates the second target portion.

The first illuminating radiation and second illuminating radiation is scattered by the first target and the second target respectively. The scattered radiation (not shown) may be detected by a detector (also not shown) and processed by a processing unit in a suitable manner. The processing unit can then be used to control the positioning of one or both of the first or second optical wedges 906, 908 in order to control the time delay of the first and/or second illuminating radiation. For example, by shifting the position of the second optical wedge but maintaining the position of the first optical wedge, the second illuminating radiation can be delayed with respect to the first illuminating radiation.

The radiation scattered radiation by the targets may be delivered to the detector of the inspection apparatus (e.g. detector 23 of FIG. 3(a)). In one example, the first scattered radiation and the second scattered radiation may be combined by a combining optical element (not shown in FIG. 3(a)) into a scattered radiation beam before being delivered to the detector. In another example, the first scattered radiation and second scattered radiation may be detected separately on the surface of the detector, and may be combined by the processing unit 940.

The detected scattered radiation is sent to a processing unit 940 (which is functionally analogous to the processing unit 40 of FIG. 3(a)). The processing unit processes the detected scattered radiation and, based on the processing results, may send correction data 932 to a correction unit 934. The correction unit comprises one or more actuating elements that are connected to one or more of the optical components of the illumination system. In the present example, the correction unit comprises an actuator 936 connected to the second optical wedge portion 908. Based on the correction data, the correction unit activates the actuator to adjust the position of the second optical wedge portion in order to control the time delay between the first illuminating radiation and the second illuminating radiation.

It will of course be appreciated that, while the first and second target structures are shown as being spatially separated in this example, the illumination system could equally well be used for overlapping target structures. In such a situation, the first and second optical wedge portions would be positioned such that the first and second illuminating radiation are incident on a single target.

Figure 9:
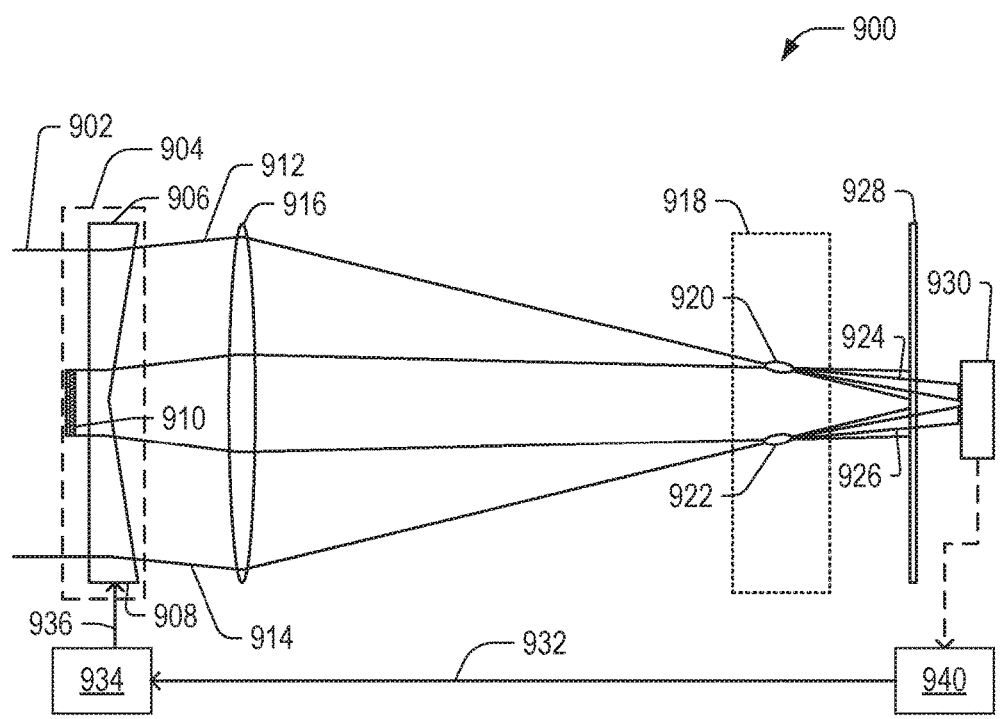
FIG. 9 illustrates an illumination system according to the first and third embodiments of the invention.

It will further be appreciated that the components of the illumination system shown in FIG. 9 are exemplary only, and that the illumination system may comprise additional or alternative components.

In the above example, the time delay is controlled by using an optical wedge for exemplary purposes only. Alternative methods or components for inducing and controlling a time delay could be envisaged by the skilled person. This includes, but is not limited to, beam-splitting prisms or interferometers. Additionally, alternative positions for the delaying component may be envisaged by the skilled person, such as positioning the delaying component in the optical path of the scattered radiation (as discussed with respect to FIG. 6 above) rather than the illuminating radiation.

Figure 10:
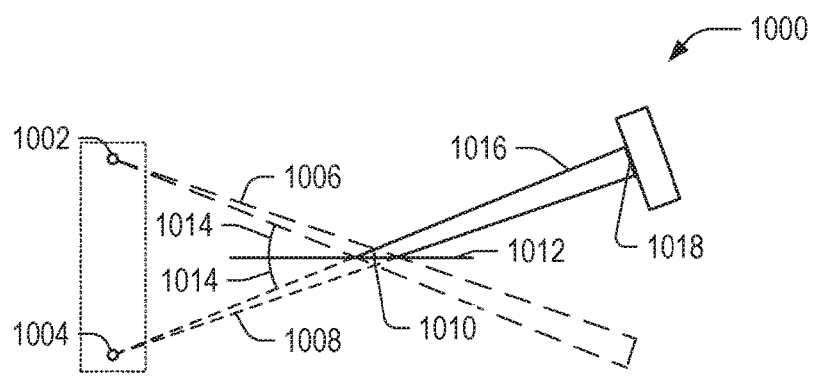
FIG. 10 illustrates an illumination system according to the first embodiment of the invention.

A second exemplary illumination system 1000 will now be discussed with reference to FIG. 10. The system comprises a first illuminating radiation source 1002 and a second illuminating radiation source 1004. The first source emits first illuminating radiation 1006, and the second source emits second illuminating radiation 1008. It is to be noted that FIG. 10 shows the first and second radiation sources only in a general sense. The first and second illuminating radiation may be generated in any suitable fashion. In one example, the first and second illuminating radiation may be generated by the illumination system 900 described in FIG. 9. In another example, the first 1002 and second 1004 sources may be physically separated but mutually coherent and "phase coupled" radiation sources. In yet another example, the first and second sources may be mutually coherent and emit radiation with a wavelength in the visible spectrum.

The first illuminating radiation 1006 and the second illuminating radiation 808 are arranged so as to be incident on a point 1010 of a surface 1012 of a combining optical element (e.g. a beamsplitter). Further, both the first illuminating radiation and the second illuminating radiation have the same angle of incidence 1014 on the surface. The first illuminating radiation is partially reflected by the surface, and the second illuminating radiation is partially transmitted through the surface. As both the first and second illuminating radiation are incident on the same point and have the same angle of incidence, the reflected portion of the first illuminating radiation and the transmitted portion of the second illuminating radiation will be combined into a combined illuminating radiation 1016. The illuminating beam is then directed towards a target structure 1018 and may be detected in a manner similar to that described above.

It will be realized that the radiation in the present example may have any suitable wavelength. In one example, the wavelength of the radiation is within the visible or near infra-red radiation spectrum.

In the above example, the combining optical element is operable to combine the first and second illuminating radiation. However, as mentioned with reference to FIG. 9, examples may be envisaged wherein the first and second scattered radiation is combined into a scattered radiation beam.

Figure 11:
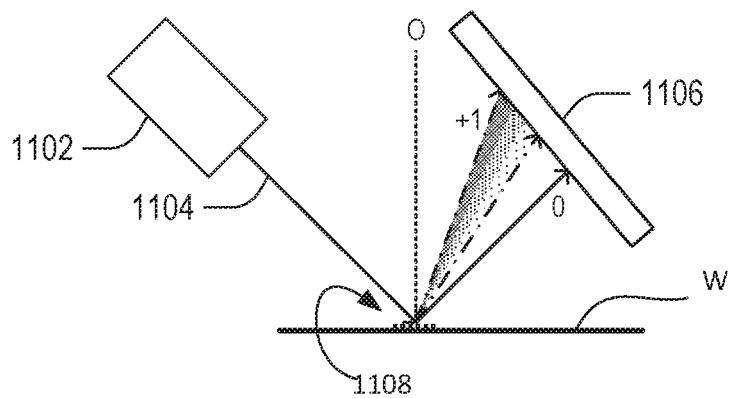
FIG. 11 is a schematic diagram of illuminating radiation and scattered radiation on a target according to a fourth embodiment of the invention.
Figure 12:
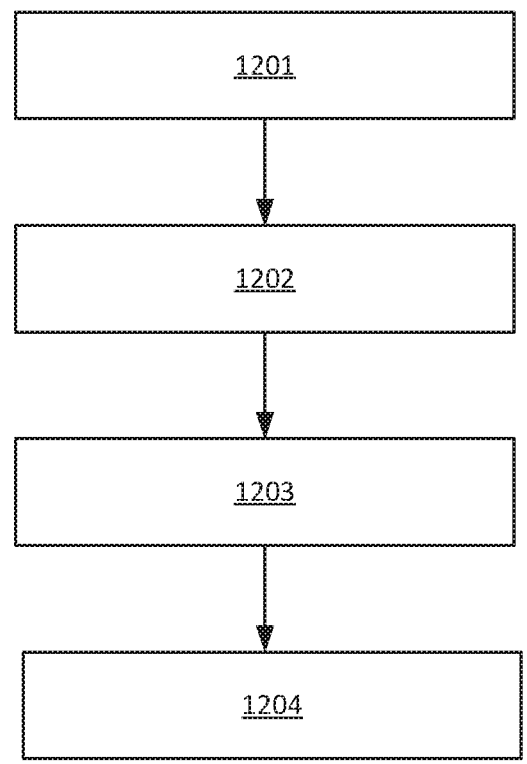
FIG. 12 illustrates a method according to the fourth embodiment of the invention.

In the above examples, the −1 and +1 diffraction orders have been used to carry out the exemplary method for performing a measurement. A further example will now be described with reference to FIGS. 11 and 12, wherein any of the diffraction orders scattered by the target may be used. The exemplary method may be implemented in a scatterometer such as the one shown in FIG. 6. As previously described, in a typical scatterometer the +1 and −1 diffraction orders of the radiation are used to determine a relevant property of the target structure (such as overlay or critical dimension).

In a first step 1201, first illuminating radiation and second illuminating radiation are provided by an illumination system 1102. In the present example, the illumination system may be any suitable source of white light, provided that it is sufficiently spatially coherent, such as a supercontinuum generated by HHG. The first and second illuminating radiation are mutually coherent, but the second illuminating radiation has a time delay relative to the first illuminating radiation. In the present example, the illumination system comprises one or more optical components for combining the first and second illuminating radiation into a combined illuminating radiation 1104. For example, the optical component may comprise the beamsplitter shown in FIG. 9.

In a second step 1202, a target structure 1108 is illuminated by the combined illuminating radiation. The combined illuminating radiation is diffracted by the target structure into a number of diffraction orders. Due to the spectral content of the combined illuminating radiation, the +1 and −1 diffraction orders are not formed as single points on the surface of the detector. Each of the wavelengths in the wavelength spectrum will be diffracted in a unique direction. The +1 and −1 diffraction orders will therefore be formed on the surface of the detector as a spatially distributed spectrums that contain all the wavelengths of the combined illuminating radiation. The 0 order radiation comprises the portion of the combined illuminating radiation that is not diffracted by the target structure, but is reflected by the target structure.

In a third step 1203, the reflected radiation beam is detected at a detector 1106. The third step comprises detecting the scattered variation using a plurality of specific time delays. The first and second reflected radiation will interfere on the surface of the detector in a manner analogous to white light interferometry. Subsequently, in a fourth step 1204, the detected radiation may be sent to a processing unit for further processing. For example, the detected interferogram may be Fourier transformed to derive the spectrally resolved 0 order reflectance by using the above-mentioned scattered variation detected using a plurality of specific time delays. It is to be noted that this method has been described using 0 order diffracted radiation, but that it may equally well be implemented using other diffraction orders (such as the −1 and +1 diffraction orders).

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin-film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

Further embodiments according to the present invention are presented in below numbered clauses:

1. A method of performing a measurement in an inspection apparatus, comprising:
providing an illumination radiation;
illuminating a target structure with the illuminating radiation resulting in at least a first and a second scattered radiation; and
detecting combined first and second scattered radiation; and
controlling a time delay between the first scattered radiation and the second scattered radiation so as to optimize a property of the combined first and second scattered radiation.
2. A method according to clause 1, wherein the target structure comprises a first target and a second target provided on a substrate, and wherein the first target and the second target substantially overlap in the plane of the substrate.
3. A method according to clause 1, wherein the target structure comprises a first target and a second target provided on a substrate, wherein the first target and the second target are spatially separated in the plane of the substrate.
4. A method according to clause 2 or 3, wherein the first scattered radiation comprises illuminating radiation scattered by the first target.
5. A method according to any of clauses 2 to 4, wherein the second scattered radiation comprises illuminating radiation scattered by the second target.
6. A method according to any previous clause, wherein the illuminating radiation comprises at least a first illuminating radiation and a second illuminating radiation.
7. A method according to clause 6, wherein the step of providing further comprises combining the first illuminating radiation and the second illuminating radiation into a combined illuminating radiation.
8. A method according to clause 7, wherein the step of illuminating comprises illuminating the target structure with the combined illuminating radiation.
9. A method according to any of clauses 6 to 8, wherein the step of providing further comprises introducing the time delay between the first illuminating radiation and the second illuminating radiation.
10. A method according to clause 9, wherein controlling the time delay comprises actuating an optical component to change the optical path of the second illuminating radiation.
11. A method according to clause 10, wherein the optical component comprises one of: an optical wedge; a beam-splitting prism; or an interferometer.
12. A method according to any previous clause, further comprising a step of combining the first scattered radiation and second scattered radiation into a combined scattered radiation.
13. A method according to clause any of clauses 7 to 12, wherein combining the first illuminating radiation and the second illuminating radiation or combining the first scattered radiation and second scattered radiation comprises using a beamsplitter to carry out the combining.
14. A method according to any previous clause, wherein the illuminating radiation has a wavelength between 1 nm and 40 nm.
15. A method according to any of clauses 1 to 13, wherein the illuminating radiation comprises radiation with a wavelength in the visible spectrum.
16. A method according to clause 15, wherein the first and second illuminating radiation comprises white light.
17. A method according to any previous clause, wherein the first and second scattered radiation comprises $1^{st}$ order diffracted radiation.
18. A method according to any of clauses 1 to 16, wherein the first and second scattered radiation comprises $0^{th}$ order diffracted radiation.
19. A method according to any previous clause, wherein controlling the characteristic comprises maximizing an intensity of the combined first and second scattered radiation.
20. An inspection apparatus operable to carry out the method of any of clauses 1 to 19.
21. An inspection apparatus according to clause 20, comprising:
a radiation source operable to provide illuminating radiation;
an illumination system operable to illuminate a target structure with the illuminating radiation resulting in at least a first and a second scattered radiation;
a detector operable to detect combined first and second scattered radiation; and
a processing unit operable to control a time delay between the first scattered radiation and the second scattered radiation so as to optimize a property of the combined first and second scattered radiation.
22. An inspection apparatus according to clause 21, wherein the target structure comprises a first target and a second target provided on a substrate, and wherein the first target and the second target substantially overlap in the plane of the substrate
23. An inspection apparatus according to clause 21, wherein the target structure comprises a first target and a second target provided on a substrate, the first target and the second target being spatially separated in the plane of the substrate.
24. An inspection apparatus according to clause 22 or 23, wherein the first scattered radiation comprises illuminating radiation scattered by the first target.
25. An inspection apparatus according to any of clauses 22 to 24, wherein the second scattered radiation comprises illuminating radiation scattered by the first target.
26. An inspection apparatus according to any of clauses 21 to 25, wherein the illuminating radiation comprises at least a first illuminating radiation and a second illuminating radiation.

27. An inspection apparatus according to clause 26, further comprising a first combining optical element operable to combine the first illuminating radiation and the second illuminating radiation into a combined illuminating radiation.
28. An inspection apparatus according to clause 27, wherein the illumination system is operable to illuminate the target structure with the combined illuminating radiation.
29. An inspection apparatus according to any of clauses 26 to 28, wherein the illumination system is further operable to introduce the time delay between the first illuminating radiation and the second illuminating radiation.
30. An inspection apparatus according to clauses 29, further comprising a correction unit operable to control the time delay by actuating an optical component of the illumination system to change the optical path of the second illuminating radiation.
31. An inspection apparatus according to clause 30, wherein the optical component comprises one of: an optical wedge; a beam-splitting prism; or an interferometer.
32. An inspection apparatus according to any of clauses 21 to 32, further comprising a second combining optical element operable to combine the first scattered radiation and the second scattered radiation into a combined scattered radiation.
33. An inspection apparatus according to any of clauses 27 to 32, wherein the first or the second combining optical element comprises a beamsplitter.
34. An inspection apparatus according to any of clauses 21 to 33, wherein the illuminating radiation has a wavelength between 1 nm and 40 nm.
35. An inspection apparatus according to any of clauses 21 to 33, wherein the illuminating radiation comprises radiation with a wavelength in the visible spectrum.
36. An inspection apparatus according to clause 35, wherein the illuminating radiation comprises white light.
37. An inspection apparatus according to any of clauses 21 to 36, wherein the detector is operable to detect $1^{st}$ order scattered radiation.
38. An inspection apparatus according to any of clauses 21 to 36, wherein the detector is operable to detect $0^{th}$ order scattered radiation.
39. An inspection apparatus according to any of clauses 21 to 36, wherein controlling the characteristic comprises maximizing an intensity of the combined first and second scattered radiation.
40. A lithographic apparatus comprising an inspection apparatus according to any of clauses 21 to 39.
41. A substrate for use in performing a measurement in an inspection apparatus, the substrate comprising a target structure usable in the method of any of clauses 1 to 19.
42. A substrate according to clause 41, wherein the target structure comprises a first target and a second target provided on a substrate, and wherein the first target and the second target substantially overlap in the plane of the substrate.
43. A substrate according to clause 41, wherein the target structure comprises a first target and a second target provided on a substrate, wherein the first target and the second target are spatially separated in the plane of the substrate.
44. A method for a lithographic apparatus for manufacturing substrates according to any of clauses 41 to 43.
45. A computer program product comprising machine readable instructions which, when run on a suitable processor, cause the processor to perform the controlling step of any of clauses 1 to 19.

The terms "radiation" and "beam" used in relation to the lithographic apparatus encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description by example, and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The invention claimed is:
1. A method comprising:
providing an illuminating radiation;
illuminating a target structure with the illuminating radiation resulting in a first scattered radiation and a second scattered radiation;
combining the first and second scattered radiation into a combined first and second scattered radiation;
detecting the combined first and second scattered radiation; and
controlling a time delay between the first scattered radiation and the second scattered radiation so as to optimize a property of the combined first and second scattered radiation.
2. The method of claim 1, wherein the illuminating radiation comprises a first illuminating radiation and a second illuminating radiation.
3. The method of claim 2, wherein the providing further comprises combining the first illuminating radiation and the second illuminating radiation into a combined illuminating radiation.
4. The method of claim 3, wherein the illuminating further comprises illuminating the target structure with the combined illuminating radiation.
5. The method of claim 3, wherein the combining the first illuminating radiation and the second illuminating radiation or the combining the first scattered radiation and second scattered radiation comprises using a beamsplitter to carry out the combining.
6. The method according of claim 2, wherein the providing further comprises introducing the time delay between the first illuminating radiation and the second illuminating radiation.

7. The method of claim 6, wherein the controlling the time delay further comprises actuating an optical component to change an optical path of the second illuminating radiation.

8. The method of claim 7, wherein the optical component comprises an optical wedge, a beam-splitting prism, or an interferometer.

9. The method of claim 1, wherein the illuminating radiation has a wavelength between 1 nm and 40 nm.

10. The method of claim 1, wherein the illuminating radiation comprises radiation with a wavelength in a visible spectrum.

11. The method of claim 10, wherein the illuminating radiation comprises white light.

12. The method of claim 1, wherein the first and second scattered radiation comprises 1st order diffracted radiation.

13. The method of claim 1, wherein the first and second scattered radiation comprises 0th order diffracted radiation.

14. The method of claim 1, wherein controlling the property comprises maximizing an intensity of the combined first and second scattered radiation.

15. The method of claim 1, wherein the controlling the time delay comprises actuating an optical component to change an optical path of the second scattered radiation.

16. An inspection apparatus comprising:
an illuminator configured to:
provide an illuminating radiation; and
illuminate a target structure with the illuminating radiation resulting in a first scattered radiation and a second scattered radiation;
an optical element configured to combine the first and second scattered radiation;
a detector configured to detect a combined first and second scattered radiation; and
a controller configured to control a time delay between the first scattered radiation and the second scattered radiation so as to optimize a property of the combined first and second scattered radiation.

17. A lithographic apparatus comprising:
an illumination system configured to produce a beam of radiation;
a patterning device configured to pattern the beam of radiation;
a projection system configured to project the patterned beam onto a substrate; and
an inspection device comprising:
an illuminator configured to:
provide an illuminating radiation; and
illuminate a target structure with the illuminating radiation resulting in a first scattered radiation and a second scattered radiation;
an optical element configured to combine the first and second scattered radiation;
a detector configured to detect a combined first and second scattered radiation; and
a controller configured to control a time delay between the first scattered radiation and the second scattered radiation so as to optimize a property of the combined first and second scattered radiation.

18. A method comprising:
providing an illuminating radiation;
illuminating a target structure with the illuminating radiation resulting in a first scattered radiation and a second scattered radiation;
combining the first and second scattered radiation into a combined first and second scattered radiation;
detecting the combined first and second scattered radiation; and
using a non-transitory computer readable medium comprising machine readable instructions which, when run on a suitable processor, cause the processor to perform operations controlling a time delay between the first scattered radiation and the second scattered radiation so as to optimize a property of the combined first and second scattered radiation.

* * * * *